(12) United States Patent
Hayashizaki et al.

(10) Patent No.: US 8,017,320 B2
(45) Date of Patent: Sep. 13, 2011

(54) METHOD OF DETECTING METASTASIZING CANCER CELLS ORIGINATING IN STOMACH CANCER

(75) Inventors: Yoshihide Hayashizaki, Tsukuba (JP); Yasushi Okazaki, Yokohama (JP); Chouhei Sakakura, Kyoto (JP); Hisakazu Yamagishi Hisakazu, Otsu (JP)

(73) Assignee: Riken, Saitama (JP)

( * ) Notice: Subject to any disclaimer, the term of this patent is extended or adjusted under 35 U.S.C. 154(b) by 1017 days.

(21) Appl. No.: 10/554,678

(22) Filed: May 14, 2008

(65) Prior Publication Data

US 2008/0293043 A1 Nov. 27, 2008

(30) Foreign Application Priority Data

Apr. 25, 2003 (JP) ................................. 2003-121780

(51) Int. Cl.
*C12Q 1/68* (2006.01)
(52) U.S. Cl. .......................................................... 435/6
(58) Field of Classification Search .................. None
See application file for complete search history.

(56) References Cited

OTHER PUBLICATIONS

Canuto et al (Biochem J., 2001, 357: 811-818).*
Tockman et al (Cancer Res., 1992, 52:2711s-2718s).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Lichtinghagen et al (European Urology, 2002, 42:398-406).*
Jelski et al (Dig Dis Sci, 2007, 52: 531-535).*
Sakakura et al (British Journal of Cancer, 2002, 87(10): 1153-1161).*
Gan To Kagakuryouhou, *Cancer and Chemotherapy*, vol. 29, No. 12, pp. 2271-2274, 2002.
Article of Japanese Cancer Association Annual Meeting, 2001, vol. 60, p. 528, #1817.
Article of Japanese Cancer Association Annual Meeting, 2002, vol. 61, p. 535, #2267.
Article of Japan Society of Clinical Oncology Annual Meeting, 2002, vol. 37, No. 2, p. 539, P037-3, P037-4.
Yokoyama et al., "Alcohol and aldehyde dehydrogenase gene polymorphisms and oropharyngolaryngeal, esophageal and stomach cancers in Japanese alcoholics," *Carcinogenesis*, 2001, vol. 22, No. 3, pp. 433-439.
GI Research, 2000, vol. 8, No. 1, pp. 56-61.
Hippo et al., "Differential Gene Expression Profiles of Scirrhous Gastric Cancer Cells with High Metastatic Potential to Peritoneum or Lymph Nodes," *Cancer Research*, 2001, vol. 61, pp. 889-895.
Japanese Office Action for corresponding to Japanese Application No. 2003-121780 dated Jan. 27, 2009.
C. Sakakura et al., "Differential gene expression profiles of gastric cancer cells established from primary tumour and malignant ascites", British Journal of Cancer, 2002, vol. 87 (10), pp. 1153 to 1161; full text.
Canuto, R.A., et al., "Increase in class 2 aldehyde dehyrogenase expression by arachidonic acid in rat hepatoma cells", Biochemical Journal, 2001, vol. 357, pp. 811 to 818; full text.
William G. North, et al., "Key Peptide processing enzymes are expressed by a variant form of small cell carcinoma of the lung", Paptides, 1998, Vol. 19(10), pp. 1743 to 1747; full text.
Jin Shun Zhi et al., "A Study of aldehyde dehydro genase in gastric mucosa", Kitasato Igaku, 1995, vol. 25(1), pp. 31 to 35; full text.
Ariyoushi T., et al., "Clinical implication of tumor marker expressions suggesting biological characters of malignancies", Nippon Rinsho. Journal of Clinical Medicine, 1996, vol. 54(6), pp. 1568 to 1573; full text.
International Search Report for PCT/JP03/14075, dated Jan. 7, 2004.

* cited by examiner

*Primary Examiner* — Sean Aeder
(74) *Attorney, Agent, or Firm* — Alston & Bird LLP

(57) ABSTRACT

Metastatic cancer cells originating from gastric cancer are detected by a method comprising the step of collecting a biological sample from a subject, the step of detecting the presence of at least either aldehyde dehydrogenase or dopa decarboxylase in the biological sample of the subject, and the step of determining that the possibility of containing metastatic cancer cells originating from the gastric cancer in the sample is high when at least either aldehyde dehydrogenase or dopa decarboxylase is present. By the use of these as markers for metastatic cancer cells originating from gastric cancer, the presence or absence of peritoneal metastasis in a gastric cancer patient can be detected rapidly and reliably, and data important for deciding whether intraperitoneal cancer chemotherapy should be applied is provided.

1 Claim, 2 Drawing Sheets

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 1
attgtgttag ctgatgccga ctt                                              23

<210> SEQ ID NO 2
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 2
cactggccct ggtggtagaa ta                                               22

<210> SEQ ID NO 3
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 3
aagcacagcc atcaggattc addc                                             24

<210> SEQ ID NO 4
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 4
tggacatgct tgcggatata ag                                               22

<210> SEQ ID NO 5
<211> LENGTH: 77
<212> TYPE: DNA
```

```
<213> ORGANISM: Artificial sequence
<220> FEATURE:
<223> OTHER INFORMATION: Oligonucleotide probe

<400> SEQUENCE: 5
cactggccct ggtggtagaa taccccatgg tgtgcaaatt caacagcatt gtccaagtcg    60
gcatcagcta acacaat                                                  77

<210> SEQ ID NO 6
<211> LENGTH: 149
<212> TYPE: DNA
<213> ORGANISM: Artificial sequence
<220> FEATURE:
<223> OTHER INFORMATION: Oligonucleotide probe

<400> SEQUENCE: 6
aagcacagcc atcaggattc agggcttatc actgactacc ggcattggca gataccactg    60
ggcagaagat ttcgctcttt gaaaatgtgg tttgtattta ggatgtatgg agtcaaagga   120
ctgcaggctt atatccgcaa gcatgtcca                                    149

<210> SEQ ID NO 7
<211> LENGTH: 23
<212> TYPE: DNA
<213> ORGANISM: Artificial sequence
<220> FEATURE:
<223> OTHER INFORMATION: Oligonucleotide primer

<400> SEQUENCE: 7
attgtgttag ctgatgccga ctt                                           23

<210> SEQ ID NO 8
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 8
cactggccct ggtggtagaa ta                                            22

<210> SEQ ID NO 9
<211> LENGTH: 21
<212> TYPE: DNA
<213> ORGANISM: Artificial sequence
<220> FEATURE:
<223> OTHER INFORMATION: Oligonucleotide primer

<400> SEQUENCE: 9
aagcacagcc atcaggattc a                                             21

<210> SEQ ID NO 10
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 10
tggacatgct tgcggatata ag                                            22
```

METHOD OF DETECTING METASTASIZING CANCER CELLS ORIGINATING IN STOMACH CANCER

REFERENCE TO A SEQUENCE LISTING SUBMITTED AS A TEXT FILE VIA EFS-WEB

The official copy of the sequence listing is submitted on Jun. 18, 2008 as a text file via EFS-Web, in compliance with the American Standard Code for Information Interchange (ASCII), with a file name of 301942_SequenceListing.txt, a creation date of Jun. 13, 2008, and a size of 3 KB. The sequence listing filed via EFS-Web is part of the specification and is hereby incorporated in its entirety by reference herein

TECHNICAL FIELD

The present invention relates to a method for detection of metastatic cancer cells originating from gastric cancer, and more specifically to a method for detection of metastatic cancer cells originating from gastric cancer such as peritoneal dissemination of gastric cancer or peritoneal free cancer cells with the use of aldehyde dehydrogenase or dopa decarboxylase as a marker.

BACKGROUND ART

Gastric cancer is the most common malignant tumor found in the gastrointestinal tract in Japan and Southeast Asia, and gastric cancer ranks in second place in cancer mortality in the world (Parkin et al. 1999). Although the prognosis for gastric cancer has improved by developments in diagnostic techniques and treatment methods of gastric cancer, the main cause of recurrence that occurs after curative resection of the advanced cancer is peritoneal dissemination. As to the prognosis for gastric cancer that has invaded to the gastric serosa, the 5-year survival rate is as low as 35% (Yamazaki et al. 1989). In such malignant properties of gastric cancer cells, metastasis to the peritoneum is a particularly complex phenomenon, which involves many steps and numerous genes. There are reports suggesting that adhesion molecules, apoptosis-related genes, and other genes are deeply involved in peritoneal dissemination of gastric cancer (Tahara et al., 1996, 2000; Yawata et al., 1998). However, elucidation of the mechanism of gastric cancer metastasis needs further investigations. Although it is known that escape of primary tumor cells from the basal layer and resistance to apoptosis are enhanced by changes in expression of genes that are suspected to be related to metastatic potential of cancer, the details of the mechanism are still unknown.

In order to study the mechanism of peritoneal dissemination of gastric cancer, Park et al. established SNU-1, SNU-5, SNU-16, and SNU-719 cell lines from the primary focus and other cancer cell lines from ascites fluid (Park et al., 1990, 1994). SNU cell lines have been studied particularly intensively. For example, it has been confirmed that cMET is amplified in SNU-16, overexpression of TGF-β2-type receptor, CEA, CA19-9, and c-erbB2 is observed in SNU-1, SNU-5, and SNU-16, K-sam is amplified in KATO-III cells (Katoh et al., 1992), and expression of E-cadherin is reduced in GT3TKB (Tamura et al., 1996). However, common gene changes in metastatic gastric cancer cells have not yet been clarified.

Despite the fact that a plurality of genes are known to participate cooperatively in cancer metastasis, only the relationship between a single gene or a few genes and metastasis has been reported. Further, the difference of metastatic potential of primary cancer focus is considered to be due to a difference in combination of expressed genes. For this reason, an analysis of gene expression in gastric cancer cells having different metastatic potential in respect of the degree of metastasis and metastasized sites is important for elucidation of the mechanism of peritoneal dissemination of gastric cancer.

DISCLOSURE OF THE INVENTION

To improve the prognosis for gastric cancer, the inventors have developed a prevention for recurrence of gastric cancer with positive serosal invasion by intraperitoneal administration of mitomycin C adsorbed on activated charcoal particles (MMC-CH). However, intraperitoneal cancer chemotherapy such as MMC-CH is associated with side effects such as thrombocytopenia and ileus. Therefore, it is necessary to confirm the possibility of metastasis of gastric cancer cells to the peritoneal cavity and rapidly determine whether the peritoneal cancer chemotherapy should be applied or not.

For the diagnosis of cancer of the digestive system, CEA (carcinoembryonic antigen) is generally used as a marker, and the use of rapid quantitative RT-PCR analysis using this as an indicator for detection of peritoneal free cancer cells has been domestically proposed by Aichi Cancer Center, etc. However, since this marker is weakly expressed in normal epidermal cells and mesothelial cells, there are many cases of false-positive determination, thus presenting a problem in detection of cancer cells in the peritoneal cavity.

Hence, the present invention aims to identify a new marker having high specificity for detection of metastatic cancer cells originating from gastric cancer such as peritoneal dissemination of gastric cancer or peritoneal free cancer cells.

In order to find a highly specific marker to rapidly determine whether or not gastric cancer is metastatic to the peritoneal cavity, the inventors analyzed expression profiles of about 21,000 genes in cell lines derived from peritoneally disseminated gastric cancer, SNU-5, SNU-16, SNU-719, KATO-III and GT3TKB cells, with the use of a cDNA microarray. As the control, a cell line derived from primary gastric cancer focus, SNU-1, was used. About 20 genes that showed highly specific expressions in the cells derived from peritoneally disseminated gastric cancer but showed no expressions or extremely weak expressions in the cells derived from primary focus of gastric cancer were identified.

Further, it was studied whether or not the above 20 genes specific for the cells derived from peritoneally disseminated gastric cancer could be applied to diagnosis of the presence of minute cancer cells in the peritoneal cavity and rapid intraoperative diagnosis thereof by combining the change in gene expression and an analysis by Northern blotting or RT-PCR. The results identified genes having sensitivity and specificity equal to or higher than CEA.

The inventors have identified aldehyde dehydrogenase (ALDH) and dopa decarboxylase (DDC) as genes that are not expressed in the cells of primary focus of gastric cancer but are specifically expressed in the cells derived from peritoneally disseminated gastric cancer, and have found that these genes can be used as detection markers of metastatic cancer cells originating from gastric cancer.

Accordingly, the present invention provides a method for detection of metastatic cancer cells originating from gastric cancer that includes the step of collecting a biological sample from a subject, the step of detecting the presence of at least either aldehyde dehydrogenase or dopa decarboxylase from the biological sample of the subject, and the step of determining that the possibility of containing metastatic cancer cells originating from gastric cancer in the sample is high when at least either aldehyde dehydrogenase or dopa decarboxylase is present.

Here, "aldehyde dehydrogenase or dopa decarboxylase is present" means that at least genes encoding these enzymes are transcribed into mRNAs, and as a matter of course, includes a case where these are translated into proteins.

It is possible to detect peritoneally disseminated gastric cancer cells in a biological sample of a subject such as ascites fluid or intraoperative peritoneal lavage cells with high detection sensitivity by using aldehyde dehydrogenase, dopa decarboxylase, or both of aldehyde dehydrogenase and dopa decarboxylase as detection markers for metastatic cancer originating from gastric cancer such as peritoneal dissemination.

Expression of aldehyde dehydrogenase or dopa decarboxylase can be confirmed by the presence of their mRNAs. The presence or absence of mRNA of aldehyde dehydrogenase or dopa decarboxylase can be confirmed with the use of primers or a probe. As the primers to confirm the presence of mRNA of aldehyde dehydrogenase, a pair of primers according to SEQ ID NO:1 and SEQ ID NO:2 can be shown as an example, and as the primers to confirm the presence of mRNA of dopa decarboxylase, a pair of primers according to SEQ ID NO:3 and SEQ ID NO:4 can be shown as an example. As the probe to confirm the presence of mRNA of aldehyde dehydrogenase, a probe according to SEQ ID NO:5 can be shown as an example, and as the probe to confirm the presence of mRNA of dopa decarboxylase, a probe according to SEQ ID NO:6 can be shown as an example.

As an alternative method, the presence of aldehyde dehydrogenase or dopa decarboxylase can be detected with the use of an antibody.

Further, the present invention provides primers to detect the presence of mRNA of aldehyde dehydrogenase or dopa decarboxylase, for example, the pair of primers according to SEQ ID NO:1 and SEQ ID NO:2, or SEQ ID NO:3 and SEQ ID NO:4. Furthermore, the present invention provides a probe to detect the presence of mRNA of aldehyde dehydrogenase or dopa decarboxylase, for example, the probe according to SEQ ID NO:5 or SEQ ID NO:6. Still further, the present invention provides an antibody to detect aldehyde dehydrogenase or dopa decarboxylase.

With the use of these primers and probes or antibodies, or a diagnostic kit containing them, it is possible to detect rapidly and reliably the presence or absence of peritoneal metastasis of a subject, particularly a gastric cancer patient, by detecting aldehyde dehydrogenase, dopa decarboxylase, or both of aldehyde dehydrogenase and dopa decarboxylase at their mRNA levels or protein levels, and data important for deciding whether intraperitoneal cancer chemotherapy should be applied or not is provided.

The biological sample of a subject is not particularly limited as long as it is derived from the peritoneal cavity, and specifically exemplified by celiac tissues such as peritoneum of the subject, ascites fluid, cells contained in intraoperative peritoneal lavage, and peritoneal lavage fluid (lavage fluid recovered after subjecting to peritoneal lavage). Particularly, ascites fluid, cells in intraoperative peritoneal lavage, and peritoneal lavage fluid are preferred because these are easy to obtain. It should be noted that cancer cells that originated from primary gastric cancer cells and metastasized to the peritoneal cavity are collectively called "metastatic cancer cells" in the present specification. The metastatic cancer cells include, for example, peritoneal free cancer cells, cancer cells in ascites fluid of gastric cancer, peritoneal dissemination, and the like. Subject means patient, particularly cancer patient, and preferably patient suspected of peritoneal metastasis of gastric cancer.

Aldehyde dehydrogenase is known as a protein related to cell defense mechanism against intra- and extracellular aldehyde, and expression in normal hepatocytes and hepatocarcinoma has been reported (Canuto et al., 2001; Deichmann et al., 1999; Canuto et al., 2001). Further, dopa decarboxylase is sometimes called aromatic L-amino acid decarboxylase, distributed in various tissues such as the kidney, liver, and brain, and involved in the biosynthetic pathway of physiologically active amines, for example, synthesis of neurotransmitters, dopamine and serotonin. High expression of dopa decarboxylase in neuroblastoma and small cell carcinoma of the lung has been reported (North et al., 1998; Gilbert et al., 1999). Although some reports on aldehyde dehydrogenase or dopa decarboxylase in cancers other than gastric cancer can be found, the expression in gastric cancer has not been reported. In addition, there is no report suggesting that aldehyde dehydrogenase or dopa decarboxylase can be used as a marker for cancers including gastric cancer.

To detect peritoneally disseminated cells or cancer cells in ascites fluid of gastric cancer, the present invention makes use of aldehyde dehydrogenase, dopa decarboxylase, or aldehyde dehydrogenase and dopa decarboxylase as a marker, and the detection of aldehyde dehydrogenase or dopa decarboxylase can be carried out either at mRNA level or at protein level.

Although the detection at mRNA level can make use of various methods such as Northern blot method, RT-PCR method, TaqMan PCR method, and a combination thereof, mRNA can be measured quantitatively and qualitatively by an arbitrary method without being particularly restricted to these methods. For example, a probe to detect mRNA of aldehyde dehydrogenase by Northern blot includes 5' CACTGGCCCTGGTGGTAGAATAC-CCCATGGTGTGCAAATTCAACAGCATT GTC-CAAGTCGGCATCAGCTAACACAAT3' (SEQ ID NO:5), and a probe to detect mRNA of dopa decarboxylase by Northern blot includes 5'-AAGCACAGCCATCAGGAT-TCAGGGCTTATCACTGACTACCGGCATTGG CAGATACCACTGGGCAGAA-GATTTCGCTCTTTGAAAATGTGGTTTGTATT TAG-GATGTATGGAGTCAAAGGACTGCAGGCT-TATATCCGCAAGCATGTCC A-3' (SEQ ID NO:6), respectively.

The detection of mRNA can be performed with the use of an appropriate probe. Here, the probe of the present invention is acceptable as long as it has a sequence that is substantially complementary to part of mRNA sequence of aldehyde dehydrogenase or dopa decarboxylase, and the length of the probe sequence, to which part of mRNA the probe is substantially complementary, and the like are not particularly restricted. Here, substantially complementary means being complementary to a degree that allows the probe to hybridize specifically to mRNA of aldehyde dehydrogenase or dopa decarboxylase. Further, even if these probes contain sequences that are non-complementary to the mRNA sequence of aldehyde dehydrogenase or dopa decarboxylase on either the 5' side or the 3' side, or both, these may be included in the probe of the present invention as long as they are able to specifically hybridize to the mRNA. For example, a probe added with an arbitrary sequence for easy detection can be used. Furthermore, a probe labeled at the 5' end for easy detection can be used, and for such a label, for example, biotin, fluorescence, $^{32}$P, or the like can be exemplified.

The primers of the present invention are appropriate as long as they are a pair of primers that are substantially complementary to part of the upstream and downstream sequences of mRNA or cDNA of aldehyde dehydrogenase or dopa decarboxylase, and the length of the primer sequence, to which part of mRNA or cDNA they are substantially complementary, and the like are not particularly restricted. Here, substantially complementary means being complementary to a degree that allows hybridization to mRNA or cDNA. For example, even if these primers contain sequences that are partially noncomplementary to the mRNA or cDNA sequence of aldehyde dehydrogenase or dopa decarboxylase on either the 5' side or the 3' side, or both, these may be included in the primers of the present invention as long as they are able to hybridize to the mRNA or cDNA. Further, primers having a mismatch sequence that is noncomplementary to these mRNAs and cDNAs can be used for prevention of non-specific amplification or introduction of an appropriate recognition site for a restriction enzyme.

An example of the primers for detection of aldehyde dehydrogenase includes a pair of primers having sequences of SEQ ID NO:1 and SEQ ID NO:2, and an example of the primers for detection of dopa decarboxylase includes a pair of primers having sequences of SEQ ID NO:3 and SEQ ID NO:4.

An example of the probe for detection of aldehyde dehydrogenase includes a probe having a sequence of SEQ ID NO:5, and an example of the probe for detection of dopa decarboxylase includes a probe having a sequence of SEQ ID NO:6.

In the detection at protein level, the detection can be performed with the use of an antibody. A monoclonal antibody, polyclonal antibody, chimeric antibody, single-chain antibody, antigen-binding fragment thereof, or the like against aldehyde dehydrogenase or dopa decarboxylase can be used, and it is more preferred to use a monoclonal antibody in view of high specificity.

The above various antibodies can be prepared by methods known to persons skilled in the art. For example, a polyclonal antibody or a monoclonal antibody is prepared by conducting commonly practiced immunization of an animal such as a rabbit, goat, sheep, mouse, rat, guinea pig, or chicken with aldehyde dehydrogenase, dopa decarboxylase, or a partial polypeptide thereof as an antigen. For the preparation of monoclonal antibody, usually a hybridoma method in which myeloma and spleen cells are fused to produce hybridoma or various modification methods thereof can be used.

It is preferred to label an antibody for easy detection. For example, labeling with a fluorescent label (FITC, etc.), fluorine-chromium label, enzyme label (horse radish peroxidase, alkaline phosphatase, β-galactosidase, phycoerythrin, etc.), radiolabel (32P, 125I, etc.), biotin label, green fluorescent protein (GFP), gold colloid label, or the like is included.

For detection of protein, various methods such as Western blot method, dot blot method, ELISA, IDAT method, SDS-PAGE, Ouchterlony analysis, immunoelectrophoresis, and a combination thereof can be used, but quantitative and qualitative measurement of protein can be performed by any arbitrary method without being limited to these methods.

Note that the presence of aldehyde dehydrogenase or dopa decarboxylase can also be detected by measurement of enzyme activity and the like.

The detection of mRNA or protein of aldehyde dehydrogenase or dopa decarboxylase can be conducted by a method known to persons skilled in the art (for example, refer to "New Gene Technology Handbook (Shin Idenshikougaku Handbook)", 3rd Ed. Matsumura, M. and Yamamoto, T., eds., Sep. 10, 1999, Yodosha Co. Ltd.)(in Japanese).

For the determination of the presence or absence of peritoneal dissemination in a subject, mRNA or protein of aldehyde dehydrogenase or dopa decarboxylase is detected in a biological sample of the subject. If necessary, information for determining whether or not peritoneal metastasis is occurring may be obtained by measuring both levels of mRNA and protein.

The diagnostic kit may include an arbitrary reagent, buffer solution, container, and the like depending on a detection method employed in addition to a probe, primers, or an antibody. For example, a reverse transcriptase, buffer solution, dNTP, Taq polymerase, and the like are included for RT-PCR.

According to the present invention, aldehyde dehydrogenase, dopa decarboxylase, or both of them can be used as markers for detection of peritoneal free cancer cells that can be applied to diagnosis of the presence of minute cancer cells in the peritoneal cavity and rapid intraoperative diagnosis. Aldehyde dehydrogenase or dopa decarboxylase is not expressed in normal epithelial cells and mesothelial cells in contrast with CEA that has been conventionally used as a detection marker, and therefore, peritoneal free cancer can be detected with high specificity and high accuracy by detecting expression of aldehyde dehydrogenase or dopa decarboxylase. The presence or absence of peritoneal dissemination of a subject is detected with high accuracy by examining the presence or absence of expression of aldehyde dehydrogenase or dopa decarboxylase, thereby allowing it to be used as one of the guidelines for whether or not subsequent intraperitoneal cancer chemotherapy is performed.

BEST MODE FOR CARRYING OUT THE INVENTION

Figure 1:
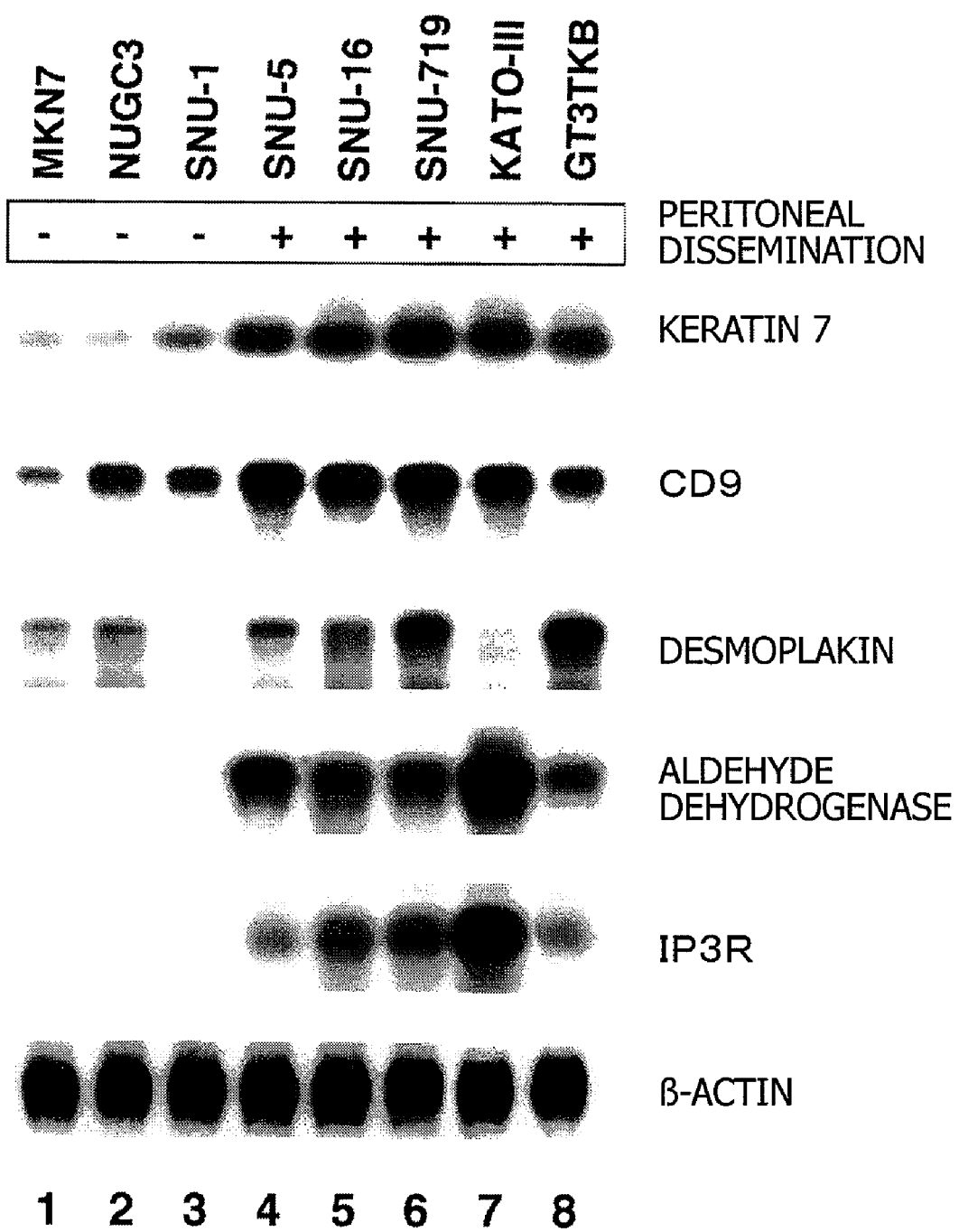
FIG. 1 shows results of Northern blot analysis of genes upregulated in cells derived from peritoneally disseminated gastric cancer compared with a primary focus.

Hereinafter, the present invention will be explained further in detail by means of the following examples, but these are in no way intended to limit the present invention.

Example 1

Gene Expression Analysis of Gastric Cancer Cells Obtained from Ascites Fluid by cDNA Microarray With the use of a high density cDNA microarray, expressions of 21,168 genes in cell lines derived from peritoneally disseminated gastric cancer and cell lines derived from primary focus of gastric cancer were analyzed, and their gene expression profiles were compared.

Gastric cancer cell lines SNU-1, SNU-5, SNU-16, and SNU-719 were established by Park et al. KATO-III and GT3TKB were purchased from RIKEN Cell Bank (Tsukuba, Japan). Among these cells, SNU-5, SNU-16, SNU-719, KATO-III and GT3TKB are cell lines derived from peritoneally disseminated gastric cancer, and SNU-1 is a cell line derived from primary focus of gastric cancer. GT3TKB was maintained in a high glucose DMEM (Sigma, St. Louis, Mo.) in an atmosphere of 5% $CO_2$ at 37 degrees C. at constant humidity. To the DMEM were added 10% fetal calf serum, penicillin, and streptomycin. After grown to 80 to 90% confluence, the cells were washed with cold PBS and homogenized promptly. mRNA extracted from each cell line was purified with FAST track kit Ver. 2 (Invitrogen) according to the instruction manual.

The preparation of a probe was carried out as follows. 1 μg of mRNA that was purified from each cell line was labeled by allowing Cy3 to be incorporated during random primed reverse transcription. cDNA obtained from each cell line of gastric cancer was labeled with Cy5 and used as an expression reference for all tissues. mRNA from 30 samples of normal gastric mucosa was used as a control. The labeling was carried out for one hour at 42 degrees C. in a total volume of 30 μl containing 400 units of SuperScript II (GIBCO/BRL), 0.1 mM CY3-dUTP (or Cy5-dUTP), 0.5 mM dATP, dCTP, and dGTP, respectively, 0.2 mM dTTP, 10 mM DTT, 6 μl of 5× first strand-buffer, and 6 μg of random primers. To remove unnecessary nucleotides, the labeled cDNA was mixed with 500 μl of a binding buffer (5 M guanidine thiocyanate/10 mM Tris-HCl, pH 7.0/0.1 mM EDTA containing 0.03% gelatin and 2 ng/μl of tRNA) and 50 μl of a silica matrix buffer (10% matrix/3.5 M guanidine hydrochloride/20% glycerol/0.1 mM EDTA/200 mM NaOAc, pH 4.8 to 5.0), passed through a GFX column (Amersham Pharmacia), and centrifuged for 30 min at 15,000 rpm using a Sorvall centrifuge (RC-3B plus; H6000A/HBB6 rotor). The effluent was discarded, and the column was washed with 500 μl of a washing buffer. The adsorbed probe was eluted in a final volume of 17 μl distilled water. This labeled probe was mixed with 3 μl of a blocking solution (10 μg/μl oligo(dA), 3 μl of 20 μg/μl yeast tRNA, 1 μl of 20 μg/μl mouse Cot1 DNA, 5.1 μl of 20×SSC, and 0.9 μl of 10% SDS) (Miki et al., 2001).

Array hybridization and data analysis were performed as follows. RIKEN cDNA containing a target was hybridized to a complete array consisting of three multiblocks in a final volume of 30 μl (each of the multiblocks requires 10 μl of hybridization solution). Prior to the hybridization, an aliquot of the probe was heated for 1 minute at 95 degrees C. and then returned to room temperature. Cover slips were hybridized at 65 degrees C. in a Hybricasette (obtained from ArrayIt.Com). After the hybridization, the slides were washed in 2×SSC/0.1% SDS until the cover slips came off, then transferred into 1×SSC, stirred gently for 2 min, and washed with 0.1×SSC for 2 min. After the washing, the slides were centrifuged in the Sorvall centrifuge (RC-3B plus; H6000A/HBB6 rotor) at 800 rpm. These slides were scanned by a ScanArray 5000 confocal laser scanner, and the obtained images were analyzed using IMAGENE (BioDiscovery: Los Angeles).

To enhance data accuracy, two experiments were performed in which the same RNA templates were labeled in two separate reactions. Unless the data was zero, it was standardized with respect to the reference standard by subtracting a median observed value (log space). Only the data points that were reproducible were employed. To exclude data with low reliability, genes that were determined not to be expressed in both cell lines of the cell lines derived from peritoneally disseminated gastric cancer and the cell lines derived from primary focus of gastric cancer from the result of software analysis were excluded.

Among the 11,680 to 15,151 genes expressed, 44 genes showed two fold higher expressions compared with their expressions in SNU-1 that was the control, and 30 genes showed more than half of expressions in other cell lines. To confirm these results, all genes that showed two fold higher expression in the cDNA array were analyzed by performing Northern blot analysis.

Northern blot was carried out by the method reported previously by the present inventors (Sakakura et al., 1994, 1996). To explain it simply, the total cellular RNA was prepared by the guanidine isothiocyanate-phenol-chloroform method. The selection of poly(A)+RNA was conducted with an oligo dT column and fractionated on 1% agarose/2.2 M formaldehyde gel. Probes labeled with $^{32}$P by means of random priming were used. Each selected gene and β-actin were hybridized to the probes. Each blot was subjected to signal analysis by a BAS 2000 image analyzer, and a rate of overexpression was calculated by comparing with SNU-1 that was a control.

When a two fold or higher change in expression level determined by the Northern blot analysis was considered to be significant, its consistency with cDNA microarray was 55% (41 genes out of 74 genes), while 27% (20 genes out of 74 genes) did not show significant changes and 18% (13 genes out of 74 genes) yielded results inconsistent with those obtained by the cDNA microarray. The genes analyzed by the microarray and Northern blot analyses are summarized in Table 1 and 2.

TABLE 1

Genes upregulated in the cells derived from peritoneally disseminated gastric cancer compared with the primary focus

| No. | GeneBank (Accession No.) | Northern blot (Average value) | Gene chip (Average value) | Gene name | Function |
| --- | --- | --- | --- | --- | --- |
| 1 | AA486275 | 3.2 | 3.63 | Leukocyte elastase inhibitor | Apoptosis |
| 2 | AA446222 | 5.7 | 4.29 | TGF-β-induced anti-apoptosis factor | Apoptosis |
| 3 | AA424695 | 2.3 | 2.14 | Integrin α3 | Cell adhesion |
| 4 | AA444051 | 3.3 | 2.58 | S100A10 (annexin II ligand) | Cell adhesion |
| 5 | AA630328 | 4.3 | 6.02 | Galectin 3 (lectin) | Cell adhesion |
| 6 | H94471 | 2.1 | 7.84 | Occludin | Cell adhesion |
| 7 | AA282906 | 6.5 | 9.58 | CD44 | Cell adhesion |
| 8 | R33456 | 7.3 | 15.89 | Desmoplakin (DP I, DP II) | Cell adhesion |
| 9 | H44051 | 6.5 | 10.48 | Keratin 14 | Cell adhesion, invasion |
| 10 | AA598517 | 15.9 | 13.64 | Keratin 8 | Cell adhesion, invasion |
| 11 | AA489569 | 10.3 | 25.63 | Keratin 7 | Cell adhesion, invasion |
| 12 | R93124 | 15.3 | 24.08 | Aldo-keto reductase family 1 | Drug metabolism |
| 13 | AA664101 | 14.7 | 33.13 | Aldehyde dehydrogenase | Drug metabolism |
| 14 | N77779 | 2.5 | 5.78 | Renal tumor antigen RAGE 1 | Immune response |
| 15 | AA424824 | 3.1 | 4.29 | Destrin (actin depolymerization factor) | Interaction with ECM |
| 16 | AA625890 | 3.8 | 7.46 | Myosin 6 | Intracellular organelle transportation |
| 17 | AA425938 | 3.1 | 2.3 | Cysteine protease (legumain) | Invsion |
| 18 | H22826 | 4.1 | 5.66 | LMO 7 | Signal transduction |
| 19 | AA496691 | 5.1 | 6.19 | Dystroglycan 1 | Signal transduction |

TABLE 1-continued

Genes upregulated in the cells derived from peritoneally disseminated gastric cancer compared with the primary focus

| No. | GeneBank (Accession No.) | Northern blot (Average value) | Gene chip (Average value) | Gene name | Function |
|---|---|---|---|---|---|
| 20 | AA455369 | 4.2 | 2.55 | Sodium/hydrogen exchange transporter, isoform 1 | Signal transduction |
| 21 | AA281735 | 11.4 | 15.56 | Inositol triphosphate receptor | Signal transduction |
| 22 | AA412053 | 7.8 | 16.34 | CD 9 | Signal transduction |
| 23 | AA25319 | 3.1 | 2.27 | Caveolin 3 | Signal transduction (modification) |
| 24 | AA702640 | 7.6 | 11.08 | Dopa decarboxylase | Signal transduction or progression |

TABLE 2

Genes downregulated in the cells derived from peritoneally disseminated gastric cancer compared with the primary focus

| No. | GeneBank (Accession No.) | Northern blot (Average value) | Gene chip (Average value) | Gene name | Function |
|---|---|---|---|---|---|
| 1 | AA453105 | 0.5 | 0.29 | H2 histone family member L | Apoptosis |
| 2 | AA025275 | 0.3 | 0.35 | Cell death-related protein | Apoptosis |
| 3 | AA485668 | 0.3 | 0.37 | Integrin β4 | Cell adhesion |
| 4 | H37989 | 0.2 | 0.52 | Tublin β-1 chain | Cell structure |
| 5 | T97593 | 0.2 | 0.37 | hnRNP | Cell structure |
| 6 | T64150 | 0.4 | 0.46 | RAD51 homolog C | Chromosome maintenance |
| 7 | H79047 | 0.3 | 0.16 | IGFBP2 | Proliferation and metabolism |
| 8 | N75745 | 0.2 | 0.09 | IL2 receptor γ | Immune response |
| 9 | AA476285 | 0.2 | 0.37 | CD4 | Immune response |
| 10 | T72202 | 0.3 | 0.46 | IL4stat | Immune response |
| 11 | AA236617 | 0.4 | 0.37 | PIXα | Signal transduction |
| 12 | AA630082 | 0.1 | 0.41 | p27kip | Signal transduction |
| 13 | AA629692 | 0.3 | 0.46 | TCP1-containing chaperone | Signal transduction |
| 14 | W46769 | 0.2 | 0.61 | Histone deacetylase | Signal transduction |
| 15 | AA485214 | 0.2 | 0.22 | Nucleobindin | Signal transduction (Apoptosis) |
| 16 | W86653 | 0.1 | 0.11 | FKBP54 | Signal transduction |
| 17 | H96140 | 0.2 | 0.43 | Acyl-coenzyme A dehydrogenase | Signal transduction |

Example 2

Expression of Selected Genes in Eight Gastric Cancer Cell Lines

Since the peritoneal dissemination potential of the other gastric cancer cell lines was summarized in several previous reports, two other gastric cancer cell lines, MKN7 and NUGC-3, in addition to the six cell lines examined in example 1 were used to study whether genes showing a difference in expression between SNU-1 and other gastric cancer cell lines have a correlation to peritoneal dissemination potential of the gastric cancer cell lines by means of Northern blot analysis. Four cell lines, KATO-III, SNU-5, SNU-16, and SNU-719, are known to possess a high dissemination potential, and therefore, these cell lines were used for a peritoneal dissemination model using nude mice. MKN7 was purchased from RIKEN Cell Bank (Tsukuba, Japan). NUGC-3 cell was purchased from the Human Science Research Resource Bank (Osaka, Japan). MKN7 and NUGC-3 were maintained in RPMI 1640 (Sigma) supplemented with 10% fetal calf serum, penicillin, and streptomycin. The other gastric cancer cell lines were cultured as described in example 1. It was confirmed in the animal experiment that MKN7 and NUGC-3 did not metastasize to the peritoneum even four weeks after inoculation. There is no report on dissemination potential of GT3TKB in nude mouse.

Figure 2:
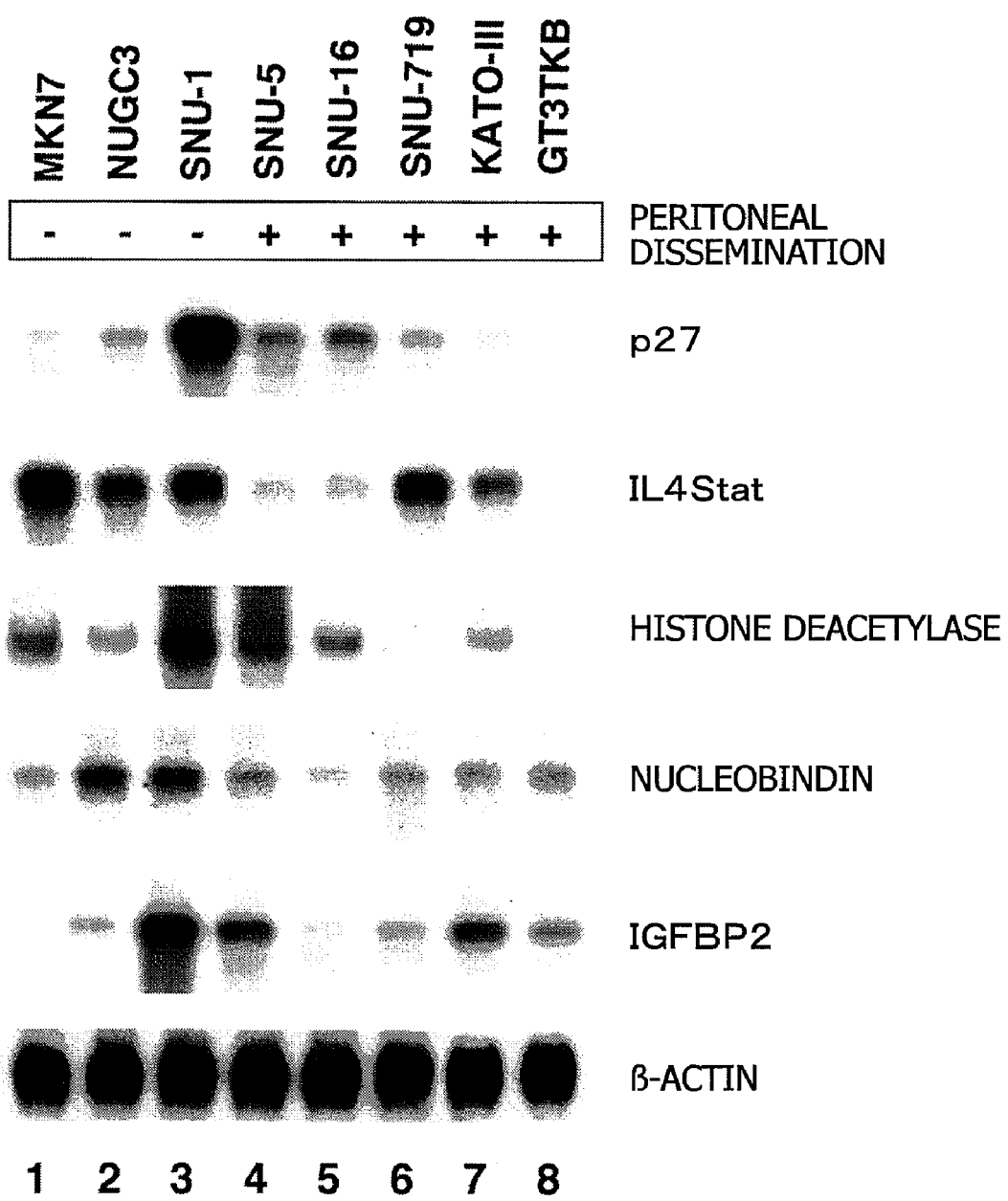
FIG. 2 shows results of Northern blot analysis of genes downregulated in the cells derived from peritoneally disseminated gastric cancer compared with the primary focus.

Northern blot analysis was carried out as described in the example 1. Typical data are summarized in FIGS. 1 and 2. FIGS. 1 and 2 are results of Northern blot analysis of genes that show different expression in eight kinds of gastric cancer cells. FIG. 1 shows genes upregulated in the cells derived from peritoneally disseminated gastric cancer compared with the primary focus. FIG. 2 shows genes downregulated in the cells derived from peritoneally disseminated gastric cancer compared with the primary focus.

From these results, it has become apparent that the cells can be classified into the following three groups: (a) cell lines with a high potential of peritoneal dissemination, SNU-5, SNU-16, SNU-719, KATO-III and GT3KTB; (b) cell line derived from tumor with no potential of dissemination, SNU-1; and (c) MKN7 and NUGC-3 with only a low potential or no potential of dissemination.

Many genes, for example, CD44 and keratin family gene, were strongly expressed in the cells derived from peritoneally disseminated gastric cancer. Genes such as aldehyde dehydrogenase and IP3R were expressed at a high level only in the cells with a high potential of dissemination, whereas these were expressed at a low level or hardly expressed in the cells with a low potential of dissemination. It seems that changes in expression levels of these genes are specific to peritoneal dissemination of gastric cancer. Many of the downregulated genes such as p27 were suppressed in all other gastric cancer cell lines, while several genes such as IL4Stat were intensively downregulated in the peritoneally disseminated gastric cancer cells.

Example 3

RT-PCR of Aldehyde Dehydrogenase and Dopa Decarboxylase in Clinical Samples From the results in examples 1 and 2, aldehyde dehydrogenase and dopa decarboxylase were not expressed in the primary gastric cancer cells or their expression levels were extremely low, while these were upregulated in the cells derived from peritoneally disseminated gastric cancer, and therefore, it was considered that an examination of these expressions might be used for the diagnosis of the presence of minute cancer cells in the peritoneal cavity. In order to confirm whether or not the expression of these genes could be applied to the diagnosis of the presence of minute cancer cells in the peritoneal cavity, the expression of aldehyde dehydrogenase and dopa decarboxylase was determined by RT-PCR in 18 patients with serosal invasion-positive gastric cancer uncertain about actual peritoneal metastasis using 12 patients with carcinomatous peritonitis of gastric cancer and 21 patients with no cancer as positive and negative controls, respectively, among cases of gastric cancer surgery performed at the Division of Digestive Surgery, Kyoto Prefectural University of Medicine.

Cells contained in cancerous ascites fluid obtained by puncture and suction from the patients with carcinomatous peritonitis of gastric cancer and in intraoperative peritoneal lavage fluid of patients with no cancer and serosal invasion-positive gastric cancer were collected by centrifugation. After extraction of RNAs by a modified AGPC method, cDNAs were synthesized using a sense primer of SEQ ID NO:7; 5'-ATTGTGTTAGCTGATGCCGACTT-3' (SEQ ID NO: 7) and an antisense primer of SEQ ID NO: 8; 5'-CACTGGC-CCTGGTGGTAGAATA-3' (SEQ ID NO:8) for aldehyde dehydrogenase and a sense primer of SEQ ID NO:9; 5'-AAG-CACAGCCATCAGGATTCA-3' (SEQ ID NO:9) and an antisense primer of SEQ ID NO:10; 5'-TGGACATGCTTGCG-GATATAAG-3' (SEQ ID NO:10) for dopa decarboxylase, respectively. With the use of these cDNAs as templates, quantitative RT-PCRs were carried out using Gene amp 5700. PCRs were carried out using a sense primer of SEQ ID NO:1; 5'-ATTGTGTTAGCTGATG CCGACTT-3' and an antisense primer of SEQ ID NO:2; 5'-CACTGGCCCTGGTGGTA-GAATA-3' for aldehyde dehydrogenase and a sense primer of SEQ ID NO:3; 5'-AAGCACAGCCATCAGGATTCADDC-AS1217 and an antisense primer of SEQ ID NO:4; 5'-TGGA-CATGCTTGCGGATATAAG-3' for dopa decarboxylase, respectively.

The results of RT-PCRs for aldehyde dehydrogenase and dopa decarboxylase are as follows:

|  | Aldehyde dehydrogenase | Dopa decarboxylase |
| --- | --- | --- |
| Specificity | 12/12(100%) | 12/12(100%) |
| Sensitivity | 19/21(95%) | 19/21(95%) |
| Serosal invasion-positive gastric cancer patient | 12/18(67%) | 16/18(67%) |

In the table, specificity indicates the number of cases where aldehyde dehydrogenase or dopa decarboxylase was detected among the 12 patients with carcinomatous peritonitis of gastric cancer, and sensitivity indicates the number of cases where aldehyde dehydrogenase or dopa decarboxylase was not detected among the 21 patients with no cancer. For the serosal invasion-positive gastric cancer patients, the number of cases where aldehyde dehydrogenase or dopa decarboxylase was detected among the 18 cases is indicated.

In the serosal invasion-positive gastric cancer patients, recurrence after that time was not confirmed; however it is inferred that the patients with aldehyde dehydrogenase or dopa decarboxylase detected have very high possibility of peritoneal metastasis.

Example 4

Sensitivity Test for Aldehyde Dehydrogenase

A sensitivity test for aldehyde dehydrogenase was performed by RT-PCR by mixing cultured mesothelial cell line or peripheral lymphocytes of normal subjects and the gastric cancer cell line SNU-5. In addition, sensitivity test for CEA was performed by mixing normal cells and the gastric cancer cell line SNU-5 and compared. Primers and conditions of RT-PCR used in the sensitivity test for aldehyde dehydrogenase were approximately the same as in example 3. In the sensitivity test for aldehyde dehydrogenase, one cancer cell in $1 \times 10^{4-5}$ normal lymphocytes could be detected, and one cancer cell in $1 \times 10^{4-5}$ cultured mesothelial cell line could be detected. When CEA was used, the detection sensitivity was such that a cancer cell could be detected in $1 \times 10^{4-5}$ normal cells. However, CEA is weakly expressed in mesothelial cells, and therefore, the detection sensitivity in mesothelial cells is significantly lowered. Thus, it can be said that aldehyde dehydrogenase has a higher sensitivity compared to CEA.

Information on prior art references related to the present application is listed as follows:

1. Canuto R A, Ferro M, Salvo R A, Bassi A M, Trombetta A, Maggiora M, Martinasso G, Lindahl R and Muzio G. (2001) Increase in class 2 aldehyde dehydrogenase expression by arachidonic acid in rat hepatoma cells. Biochem J, 357:811-8.
2. Deichmann M, Benner A, Bock M, Jackel A, Uhl K, Waldmann V and Naher H. (1999) S100-Beta, melanoma-inhibiting activity, and lactate dehydrogenase discriminate progressive from nonprogressive American Joint Committee on Cancer stage 1V melanoma. J Clin Oncol, 17:1891-6.
3. Gilbert J, Haber M, Bordow S B, Marshall G M and Norris M D. (1999) Use of tumor-specific gene expression for the differential diagnosis of neuroblastoma from other pediatric small round-cell malignancies. Am J Pathol, 155:17-21.
4. Katoh M, Hattori Y, Sasaki H, Tanaka M, Sugano K, Yazaki Y, Sugimura T and Terada M (1992) K-sam gene encodes secreted as well as transmembrane receptor tyrosine kinase. Proc Natl Acad Sci USA, 89:2960-4.
5. Miki R, Kadota K, Bono H, Mizuno Y, Tomaru Y, Caminci P, Itoh M, Shibata K, Kawai J, Konno H, Watanabe S, Sato K, Tokusumi Y, Kikuchi N, Ishii Y, Hamaguchi Y, Nishizuka I, Goto H, Nitanda H, Satomi S, Yoshiki A, Kusakabe M, DeRisi J L, Eisen M B, Iyer V R, Brown P0, Muramatsu M, Shimada H, Okazaki Y and Hayashizaki Y. (2000) Delineating developmental and metabolic pathways in vivo by expression profiling using the RIKEN set of 18,816 full-length enriched mouse cDNA arrays. Proc Natl Acad Sci USA; 98:2199-204.
6. North W G and Du J. (1998) Key peptide processing enzymes are expressed by a variant form of small-cell carcinoma of the lung. Peptides 19:1743-7.
7. Park J G, Frucht H, LaRocca R V, Bliss D P Jr, Kurita Y, Chen T R, Henslee J G, Trepel J B, Jensen R T, Johnson B E, et al. (1990) Characteristics of cell lines established from human gastric carcinoma. Cancer Res, 50:2773-80.
8. Park K, Kim S J, Bang Y J, Park J G, Kim N K, Roberts A B and Spom M B. (1994) Genetic changes in the transforming growth factor beta (TGF-beta) type II receptor gene in human gastric cancer cells: correlation with sensitivity to growth inhibition by TGF-beta. Proc Natl Acad Sci USA. 91:8772-6.

9. Parkin, D. M., Pisani, P and Ferlay, J. (1999). Estimates of the worldwide incidence of 25 major cancers in 1990. Int. J. Cancer 80, 827-841.
10. Sakakura C, Ymaguchi-Iwai Y, Satake M, Bae S C, Takahashi A, Ogawa E, Hagiwara A, Takahashi T, Murakami A, Makino K, Nakagawa A T, Kamada N and Ito Y (1994) Growth inhibition and induction of differentiation of t(8; 21) acute myeloid leukemia cells by the DNA-binding domain of PEBP2 and the AML1/MTG8(ETO)-specific antisense oligonucleotide. Proc Natl Acad Sci USA 91:11723-11727.
11. Sakakura C, Sweeney E A, Shirahama T, Igarashi Y, Hakomori S, Nakatani H, Tsujimoto H, Imanishi T, Ohgaki H M, Ohyama T, Yamazaki J and Hagiwara A, Yamaguchi T, Sawai K and Takahashi T (1996) Overexpression of bax sensitizes human breast cancer MCF-7 cells to radiation-induced apoptosis. Int J Cancer; 67:101-105.
12. Tahara E (2000) Molecular aspects of invasion and metastasis of stomach cancer Verh Dtsch Ges Patol, 84, 43-9.
13. Tahara E, Semba S and Tahara H (1996) Molecular biological observations in gastric cancer. Semin Oncol 23:307-15.
14. Tamura G, Sakata K, Nishizuka 5, Maesawa C, Suzuki Y, Iwaya T, Terashima M, Saito K and Satodate R. (1996) Inactivation of the E-cadherin gene in primary gastric carcinomas and gastric carcinoma cell lines. Jpn J Cancer Res.; 87:1153-9.
15. Yamazaki H, Oshima A, Murakami R, Endoh S and Ubukata T. A long-term follow-up study of patients with gastric cancer detected by mass screening. Cancer. 1989; 63:613-7.
16. Yawata A, Adachi M, Okuda H, Naishiro Y, Takamura T, Hareyama M, Takayama S, Reed J C. and Imai K. (1998) Prolonged cell survival enhances peritoneal dissemination of gastric cancer cells. Oncogene16, 2681-2686.

The invention claimed is:

1. A method for detection of metastatic cancer cells originating from gastric cancer, comprising the steps of:
   collecting a sample derived from the peritoneal cavity of a subject;
   detecting the presence of mRNA of aldehyde dehydrogenase in the sample from the subject; and
   determining that the possibility of containing metastatic cancer cells originating from the gastric cancer in the sample is high when mRNA of aldehyde dehydrogenase is present.

* * * * *

UNITED STATES PATENT AND TRADEMARK OFFICE
CERTIFICATE OF CORRECTION

PATENT NO. : 8,017,320 B2
APPLICATION NO. : 10/554678
DATED : September 13, 2011
INVENTOR(S) : Hayashizaki et al.

Page 1 of 1

It is certified that error appears in the above-identified patent and that said Letters Patent is hereby corrected as shown below:

On the Title page,

Delete the following:

Item "(22)   Filed: May 14, 2008"

Insert the following:

Item -- (22)    PCT Filed:    Nov. 4, 2003

(86)    PCT No.:    PCT/JP2003/014705

§371 (c)(1), (2), (4) Date:    May 14, 2008 --.

Signed and Sealed this
Tenth Day of April, 2012

David J. Kappos
*Director of the United States Patent and Trademark Office*